US005354832A

United States Patent [19]

Chang et al.

[11] Patent Number: 5,354,832

[45] Date of Patent: Oct. 11, 1994

[54] STABLE AQUEOUS DISPERSIONS CONTAINING SILOXANES FOR TREATING CELLULOSIC MATERIAL

[75] Inventors: Wen-Hsuan Chang, Gibsonia, Pa.; John F. Grunewalder, Mequon, Wis.; Mark A. Harley, Oakmont; Edward E. McEntire, Allison Park, both of Pa.

[73] Assignee: PPG Industries, Inc., Pittsburgh, Pa.

[21] Appl. No.: 48,707

[22] Filed: Apr. 16, 1993

Related U.S. Application Data

[63] Continuation of Ser. No. 775,890, Oct. 15, 1991, abandoned.

[51] Int. Cl.[5] .............................................. C08G 77/06

[52] U.S. Cl. ........................................ 528/10; 528/30; 528/41; 556/445; 106/287.16; 524/858

[58] Field of Search ..................... 106/287.16; 528/10, 528/30, 41; 556/445; 524/858

[56] References Cited

U.S. PATENT DOCUMENTS

| | | | |
|---|---|---|---|
| 3,787,467 | 1/1974 | Lucking et al. | 260/448.8 R |
| 4,429,082 | 1/1984 | Lee et al. | 525/426 |
| 4,620,878 | 11/1986 | Gee | 106/287.15 |
| 4,648,904 | 3/1987 | De Pasquale et al. | 106/2 |
| 4,927,950 | 5/1990 | Hisamoto et al. | 556/419 |
| 5,051,129 | 9/1991 | Cuthbert et al. | 106/2 |

FOREIGN PATENT DOCUMENTS

| | | |
|---|---|---|
| 278305 | 8/1988 | European Pat. Off. . |
| 340816 | 11/1989 | European Pat. Off. . |
| 2125609 | 9/1972 | France . |
| 2047296 | 11/1980 | United Kingdom . |

*Primary Examiner*—John C. Bleutge
*Assistant Examiner*—Margaret W. Glass
*Attorney, Agent, or Firm*—Linda Pingitore

[57] ABSTRACT

A stable aqueous dispersion having a particle size in the range of about 10 to about 200 nanometers containing specific silanes carrying at least one hydrophobic moiety and at least one water-solubilizing moiety is claimed along with the process for treating a cellulosic substrate and the treated cellulosic product resulting therefrom. The aqueous dispersions are stable for at least 20 days without externally added surfactant.

5 Claims, No Drawings

STABLE AQUEOUS DISPERSIONS CONTAINING SILOXANES FOR TREATING CELLULOSIC MATERIAL

This application is a continuation of application Ser. No. 07/775,890, filed Oct. 15, 1991, now abandoned.

CROSS REFERENCE TO RELATED U.S. PATENT APPLICATIONS

1. U.S. patent application Ser. No. 07/776,104, now U.S. Pat. No. 5,118,752, filed concurrently herewith, of the same inventors for "Silanes Carrying Water-Solubilizing and Hydrophobic Moieties" and 2. U.S. patent application Ser. No. 07/776,040, filed concurrently herewith, of Wen Hsuan Chang, Marvin L. Kaufman and Edward E. McEntire, for "Vinyl Polymer Latex Systems".

BACKGROUND QF THE INVENTION

1. Field of the Invention

This invention relates to (1) stable aqueous solutions (or dispersions) containing siloxanes, some of which siloxane precursors, namely the corresponding silanes, are new and novel, (2) a process for treating a cellulosic substrate, particularly a wood substrate with said stable aqueous solutions to provide said wood with long-term durability against weathering, and (3) the treated cellulosic substrate, particularly a wood substrate.

2. Description of the Prior Art

Silanes containing hydrolyzable groups, such as methoxy, for many years were believed to be unstable in the presence of a quantity of water near or even in slight excess of the amount stoichiometrically required to substantially fully hydrolyze the same. Only silanes with special structural features, i.e., aminopropylsilanes, were known to form stable aqueous solutions, that is, aqueous solutions that would not tend to form gels or precipitates upon standing over a long period of time, but these had neither hydrophobic or water-solubilizing moieties contained in the silanes used in the preparation of the stable aqueous solution claimed herein. Thus, low molecular weight silanes have been commercially employed at high dilution (generally less than about five weight percent in water) for treating inorganic fibers, as adhesion promoters to chemically bond said fibers to an organic polymer, plastic or resin, for example, as described in U.S. Pat. No. 3,973,057 to Clannin.

Part of the reason for aqueous solutions of siloxanes of low dilution may be related from the fact that it is well known that trialkoxy silanes will hydrolyze stepwise in water to give the corresponding silanols, which ultimately condense to siloxanes. See *Silane Coupling Agents,* by E. P. Plueddemann, Plenum Press, New York, N.Y., 1982, pages 32 and 33. It would be expected that since condensation results in the production of extremely large molecular siloxane entities, the latter would be expected to be insoluble or only partially soluble in water and gel formation or precipitation would occur. Therefore, as seen, for example, in U.S. Pat. No. 4,913,972 to Grunewalder et al and U.S. Pat. No. 4,386,134 to Puhringer, they use partially hydrolyzed silanes or silanes in organic solvents and speak rather vaguely of the use of water as a solvent therefor. Plueddemann, in his book referred to above, in fact is quite careful in his assessment of aqueous solutions containing siloxanes. Thus, on page 51, Section 3.22, he states that solubility of hydrolyzates containing silane triols decreases both as the hydrocarbon content of the precursor silane increases as silanols condense to oligomer silanols, but on page 58, Section 3.3.1, he states that certain amino organofunctional trialkoxysilanes, without defining any specific compounds, are readily soluble in water to give solutions of unlimited solubility without defining what such amounts of siloxanes are solubilized therein. He then says quite generally on page 60, Section 3.3.1, that if the aminoalkyl on silicon is sufficiently hydrophobic, the polysiloxanes retain water solubility, and then goes on to further solubility considerations in water that apparently are not inconsistent with the reluctance of those skilled in the art to dissolve organosilanes in water in high concentrations.

Applicants have found that they can introduce specific silanes containing both water-solubilizing and hydrophobic moieties, which silanes will be defined more specifically hereinafter, some of which are new and are claimed in our copending application identified above, in water in amounts well in excess of the amount stoichiometrically required to substantially fully hydrolyze the same, for example, concentrations from about five to about 60 percent, or even higher, to obtain aqueous stable solutions, that is, aqueous solutions that will not tend to form gels or coagulate, for a period of at least about 20 days, even upto about 300 days, or even more. Such stability is obviously highly desired, since it permits shipment of these products with a minimum freight expense, because of the high concentration of silanes therein, and also permits storage thereof over a long period of time. These aqueous solutions are, of course, not moisture sensitive as are compositions containing their organosilane precursors.

The novel stable aqueous solutions containing siloxanes, defined above, can be used to treat any cellulosic material, such as wood or composites prepared therefrom, such as defined in U.S. Pat. No. 4,913,972 of Grunewalder et al, referred to above, paper, etc., but are eminently suitable for treating wood to improve its durability to natural weathering.

Solid wood substrates for use in outdoor applications, such as in exterior building materials of various types, typically are protected from the effects of weathering by painting the wood with a conventional paint or by staining the wood with, for example, a pigmented opaque stain. While coatings which are opaque, or substantially so, can afford good protection against weathering, particularly against the combined effects of moisture and ultraviolet light, they do not allow the natural beauty of the wood, such as the grain of the wood, to be seen. It has long been desirable to provide a coating system for exterior wood which is transparent, or essentially so, and yet still affords excellent protection against weathering. However, this object has been elusive with respect to achieving relatively long term exterior durability in a transparent coating system for wood. For example, wood which has been coated with a conventional, clear coating such as a conventional air dry urethane, alkyd or spar varnish often exhibits signs of deterioration in both the coating and, more importantly, in the underlying wood itself, in as little as one year from the time of application.

It is observed in the article, "Microscale Effects of Ultraviolet Irradiation and Weathering on Redwood Surfaces and Clear Coatings," *Journal of Paint Technology,* Vol. 41, No. 531, page 275 ff, (April, 1969) that, "Most conventional clear coatings strongly absorb ultraviolet radiation, which leads to their rapid degradation. Then degradation of the wood surface beneath may follow. When clear coatings are used that are transparent to ultraviolet radiation, the coating may be very stable, but the wood surface may then be rapidly degraded. The photodegradation of the wood surface, therefore, may be an important factor in the relatively short life of clear coatings that transmit all or only a portion of the ultraviolet wavelengths of solar radiation."

Moreover, it was observed in the aforesaid article, that a silicone resin which "was known to transmit considerably more of the ultraviolet radiation that the two varnishes" (a phenolic varnish and a polyurethane varnish), offered little if any protection from degradation upon exposure to a source of ultraviolet light.

It is taught in the article, "Natural finishes for exterior timber," *Pigment and Resin Technology*, April, 1986, page 10 ff, that "Any wood exposed to sunlight and rain will in time lose its original colour. The change is due partly to loss of water-soluble extractives, which occurs quite rapidly, but mainly to the breakdown of lignin and other components in the wood by ultra-violet components in sunlight, and subsequent removal of the breakdown products by rain; and further with respect to clear varnishes as follows.

"Fully exposed varnish often has a short life, principally because of the tendency of most types to embrittle by weathering, so that in time they disintegrate under the stresses imposed by a wood substrate. Ultra-violet light can pass through the film and bleach or degrade the underlying wood surface. Many cases of premature varnish failure can be traced to detachment of this degraded wood surface layer; this is often brought about by water getting behind the film where end grain is exposed, for example at joints or unstopped nail holes, or as a result of damage."

"These shortcomings are common to all of the varnishes commonly used. Polyurethanes of the moisture-curing and two-pack types give good service indoors but the stresses within such a [sic] strong coatings are sufficient to cause peeling when the outermost layer of wood under the film become degraded; the remnants of the coating are difficult to strip either mechanically or chemically. Unless there are exceptional requirements for toughness and abrasion resistance, polyurethanes are therefore best avoided outdoors. Marine or yacht varnishes have also not been found satisfactory under conditions of full exposure on buildings."

In the article, "Chemistry of Weathering and Protection," *The Chemistry of Solid Wood,* Capter 11, published 1984 by the American Chemical Society, page 435 ff, it is taught that, "The addition of colorless UV light absorbers to clear finishes has found only moderate success to help retain the natural color and original surface structure of wood . . . Opaque pigments found in paints and stains generally provide the most effective and long-lasting protection against light . . . Even when using relatively durable, clear, synthetic resin varnishes, the weatherproof qualities of the wood-varnish system are still limited because UV light penetrates the transparent varnish film and gradually degrades the wood under it . . . Eventually, the varnish begins to flake and crack off, taking with it fibers of the wood that have been degraded photochemically . . . " [citations to references deleted].

Organosilanes have been used in the treatment of wood, for example, in U.S. Pat. No. 4,913,972 to Grunewalder et al and U.S. Pat. No. 4,386,134 to Puhringer, referred to above, as well as in U.S. Pat. No. 4,429,082 to Lee et al. However, Grunewalder et al use partially hydrolyzed organosilanes and organosilicates with organic solvents as carriers therefor, specifically toluene in the working examples. After listing many organic solvents as being useful as carriers, Grunewalder et al state that some of the organosilicon-containing compounds useful therein can be used in aqueous, rather than organic solvent borne wood treatment compositions, but neither identifies the silanes, nor the stability nor the concentration thereof in an aqueous solution. Puhringer says he impregnates wood with a silane in the form of a solution, suspension or emulsion, the continuous phase being a gas, such as air or water vapor, liquids, such as water, alcohols, such as lower alkanols with 1 to 4 carbon atoms, mixtures of water and such alcohols, light petrol, naphtha or other petroleum products, ligroin, esters, benzene, toluene, xylene, hydrocarbons and chlorinated hydrocarbons, tars, cresot oils, etc., but in the specific examples shows only the use of aqueous ethanol and does not comment on the stability of the treating solutions. Lee et al use organic solvents only, if a carrier is to be used.

The compounds of the above mentioned references also contain hydrolyzable groups, such as alkoxy groups, attached to the silicon atom. This fact renders these compounds moisture sensitive. What this means is that open containers of the silicon-containing compounds, even if dissolved in organic solvents, will react with the moisture from the air and hydrolyzed and further condense to form polymeric species. The result is that these materials are, from a practical standpoint, very difficult to use successfully. The open containers form skins on the top of the liquid, form precipitates which are particulates which tend to clog spray equipment or if applied to a surface, form rough coatings due to the particulates. The open container may even cause the components therein to gel or solidify due to hydrolysis and condensation reactions due to moisture exposure.

In view of the above, it would have been expected that since hydrolysis and condensation of the silanes would produce, in any event, large molecules, they would not be suitable for use in treating a cellulosic porous substrate, such as wood, for little or no penetration would be expected and yet herein, as will be shown hereinafter, the aqueous solutions are not only stable but can be easily applied to wood and the wood so treated will exhibit long-term durability against weathering.

The coating industry is desirous of using as little as possible of organic carriers, particularly volatile organic compounds (VOC), and, in fact carriers other than the above. Organic solvents can be toxic, they can be lost to the ambient surroundings, causing pollution problems, and they can be expensive and sometimes in short supply. For these reasons water-based coatings are desirable when they can be used in a coating operation without loss of performance of the coating medium, since water is relatively cheap, non-toxic, does not result in environmental problems, etc. Accordingly, the water-based stable solutions used herein for treating wood result in a treated wood having durability against weathering that is as good, or even better, than wood with similar type treating agents in an organic carrier.

BRIEF SUMMARY OF THE INVENTION

The novel siloxanes used herein for the preparation of stable aqueous dispersions having a particle size in the range of about 10 to about 200 nanometers suitable for treating wood can be anionic or nonionic. The anionic silanes can be defined by one of the following structural formulas:

$$R^1SiY_3 \quad (I)$$

or $$R^1R^2SiY_2, \quad (II)$$

wherein $R^1$ represents a hydrocarbon group having from about 7 to about 30 carbon atoms, preferably from about 7 to about 20, carbon atoms, such as alkyl, cycloalkyl, aryl, aralkyl and alkaryl, containing at least one hydrophobic moiety and at least one neutralized anionic water-solubilizing moiety, such as ammonia-neutralized carboxylic acid, amine-neutralized sulfonic acid, etc.;

$R^2$ represents $R^1$, H an alkyl radical having from 1 to 20 carbon atoms, preferably one to 10 carbon atoms, such as methyl, ethyl, etc., an aryl radical having from 6 to 18 carbon atoms, preferably from 6 to 10 carbon atoms, an aralkyl radical having from 7 to 20 carbon atoms, preferably from 7 to 10 carbon atoms, an alkaryl radical having from 7 to 20 carbon atoms, preferably 7 to 10 carbon atoms; and Y represents $OR^3$, wherein $R^3$ represents H, lower alkyls having from 1 to 3 carbon atoms, preferably $CH_3$ or $C_2H_5$, aryl or alkaryl radicals having from 6 to 10 carbon atoms, preferably from 6 to 7 carbon atoms or $$-\overset{O}{\overset{\|}{C}}-R^4,$$

wherein $R^4$ represents H, or a lower alkyl having from 1 to 2 carbon atoms, preferably $CH_3$.

The nonionic siloxanes used herein for the preparation of stable aqueous dispersions for treating wood can be defined by one of the following structural formulas:

$$R^5SiY_3 \quad (III)$$

or $$R^5R^6SiY_2, \quad (IV)$$

wherein $R^5$ represents a hydrocarbon group having at least 6 carbon atoms, preferably from 7 to 150 carbon atoms, such as alkyl, cycloalkyl, aryl, aralkyl and alkaryl, containing at least one hydrophobic moiety and at least one nonionic water-solubilizing moiety, such as polyoxyethylene;

$R^6$ represents $R^5$, H, an alkyl radical having from 1 to 20 carbon atoms, preferably one to 10 carbon atoms, such as methyl, ethyl, etc., an aryl radical having from 6 to 18 carbon atoms, preferably from 6 to 10 carbon atoms, an aralkyl radical having from 7 to 20 carbon atoms, preferably from 7 to 10 carbon atoms, an alkaryl radical having from 7 to 20 carbon atoms, preferably from 7 to 10 carbon atoms; and Y is as defined above.

The aqueous dispersions of the claimed invention are stable for at least 20 days without externally added surfactant.

In addition to the novel stable aqueous solutions prepared using the anionic siloxanes defined above in Compositions (I) and (II), or the nonionic siloxanes defined above in Compositions (III) and (IV), we can also treat wood in accordance with the process defined and claimed herein using stable aqueous solutions prepared using cationic siloxanes defined by one of the following structural formulas:

$$R^7SiY_3 \quad (V)$$

or $$R^7R^8SiY_2, \quad (VI)$$

wherein $R^7$ represents a hydrocarbon group having at least 7 carbon atoms, preferably from 12 to 22 carbon atoms, such as alkyl, cycloalkyl, aralkyl and aralkyl, containing at least one hydrophobic moiety and at least one cationic water-solubilizing moiety, such as quaternary ammonium acetate and terniary, sulfonium chloride;

$R^8$ represents $R^7$, H, an alkyl radical having from 1 to 20 carbon atoms, preferably one to 10 carbon atoms, such as methyl, ethyl, etc., an aryl radical having from 6 to 18 carbon atoms, preferably from 6 to 10 carbon atoms, an aralkyl radical having from 7 to 20 carbon atoms, an alkaryl radical having from 7 to 20 carbon atoms, preferably from 7 to 10 carbon atoms; and Y is as defined above.

In the above, when we speak of "hydrophobic moieties" we mean those moieties which tend to repel water and encourage micelle formation. Therefore, when we refer to $R^1$, $R^5$ and $R^7$ as representing a hydrocarbon group, such hydrocarbon group itself satisfies the requirement of a hydrophobic moiety. It is within the purview of our invention that such hydrophobic groups can contain functional groups, such as hydroxy, ether, urethane, imide, amine, amide or carbon-to-carbon double bond or halogen. By "water-solubilizing moieties", we mean those moieties which readily strongly associate with water. For Compounds (I) and (II) such moieties can be defined by one of the following structural formulas, $$-C\begin{matrix}\nearrow O\\ \searrow OX\end{matrix}, \quad (1)$$

$$-SO_3X, \quad (2)$$

$$-OSO_3X, \quad (3)$$

$$-PO_3XX_1 \quad (4)$$

and $$OPO_3XX, \quad (5)$$

wherein

X represents $NR^9R^{10}R^{11}R^{12}$, an alkali metal, such as sodium and potassium, $X_1$ represents X or H, and $R^9$, $R^{10}$, $R^{11}$ and $R^{12}$ represent H or alkyl radicals having from 1 to 3 carbon atoms, preferably 1 to 2. $R^9$ through $R^{12}$ can also contain hydroxyl.

For Compounds (III) and (IV) the water-solubilizing moieties can be represented by the following structural moiety:

$(CH_2CH_2O)_{n1}$, wherein $n_1$ is an integer ranging from about 10 to about 65, preferably about to about 55.

For Compositions V and VI the water-solubilizing moieties can be represented, for example, by the following structural formula:

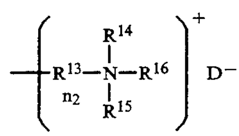

wherein $R^{13}$ represents a divalent hydrocarbon moiety having from 2 to 10 carbon atoms, preferably from 2 to 10 carbon atoms, preferably from 2 to 6, such as ethylene, propylidene, hexylidene and phenylidene;

$R^{14}$, $R^{15}$ and $R^{16}$ represent H, an aliphatic hydrocarbon radical having from 1 to 20 carbon atoms, preferably from 1 to 18 carbon atoms, or an aralkyl radical having from 7 to 20 carbon atoms, preferably from 7 to 18 carbon atoms. One or more of $R^{14}$, $R^{15}$ and $R^{16}$ can constitute the hydrophobic moiety. The total carbon atoms in $R^{14}+R^{15}+R^{16}$ should not exceed about 20, unless those radicals contain other water-solubilizing moieties, such as hydroxy, ether, protonated amine, quaternary ammonium or amide.

D represents a halide, such as chloride, bromide or iodide, preferably chloride, $$\overset{O}{\overset{\|}{OC}}-R^{17},$$

$O_3SR^{17}$ or $O_3SOR^{18}$, wherein $R^{17}$ and $R^{18}$ represent H, a lower alkyl radical having from 1 to 3 carbon atoms, preferably $CH_3$, an aryl or alkaryl radical having from 6 to 10 carbon atoms, preferably from 6 to 7 carbon atoms, optionally carrying other functional groups, such as OH, ether and amides and $R^{18}=R^{17}$ but not H; and $n_2$ is the integer 0 or 1.

When the above silanes are dissolved in water they will hydrolyze stepwise to give the corresponding silanols, which ultimately condense to siloxanes, as stated on page 3 in the Pleuddemann book referred to above:

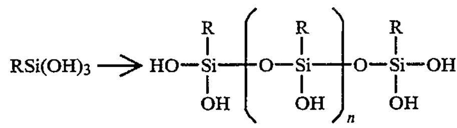

and it is the latter entity that is to be found in our stable aqueous solutions claimed herein that we use to treat cellulosic substrates, such as wood to provide such treated wood with durability against weathering for long periods of time.

In order to prepare the above aqueous siloxanes, the precursor silanes are added to water and in a matter of about five minutes to about 50 hours, the desired aqueous solution is obtained containing at least about five weight percent of the silane and its hydrolysis products, generally from about ten to about 60 weight percent of the silane and its hydrolysis products in water, wherein water is in excess of the amount stoichiometrically required to substantially fully hydrolyze the organic silane used. The process can be carried out at ambient temperature, although elevated temperatures can be used, if desired, to accelerate siloxane formation.

We believe that the silanes used herein to form the stable aqueous solutions, or dispersions, containing siloxanes will always have an HLB [hydrophilic (water-soluble moieties)-lipophilic (hydrophobic moieties) balance] of at least 10 when the same are dissolved in water, as determined by the method described in Kirk-Othmer, Encyclopedia of Chemical Technology, Third Edition, Volume 8, John Wiley & Sons, New York, N.Y. (1979) starting on page 910. HLB is an expression of the relative simultaneous attraction of a compound, for example, for water and oil (or for the two phases of the system being considered).

By "solution" we mean a clear aqueous liquid, for example water, having dissolved therein one or more compounds, for example, those defined above. By "dispersion" we mean a solid or a liquid having a particle size in the range of about 10 to about 200 nanometers homogeneously dispersed in a carrier liquid, such as water. By "hydrophobic moiety" we mean to include those moieties which are capable to repelling water and encourage micelle formation.

The stable aqueous solutions containing siloxanes defined above can be used above for treating a cellulosic substrate, particularly wood. However, there can also be present in amounts between about 0.50 to about 50 percent by weight, more preferably between about 0.50 and about 20 percent by weight, and still more preferably between about 0.50 and about 5.0 percent by weight of the composition of a water repellent. The wood treatment composition also may optionally contain between about 0.55 and about 20 percent by weight, more preferably between about 0.55 and about 6.0 percent by weight, and still more preferably between about 0.55 and about 3.0 percent by weight of a wood preservative. It should be noted that the aforesaid amounts of water repellent and wood preservative are given for the composition at end use. Of course, the percentages would be higher if the composition were in the form of a concentrate. Also, low levels of hiding pigment which can serve as a coloring agent may be incorporated into the treatment composition and/or in a composition such as a transparent stain (for example, applied to the wood substrate separately from the treatment composition).

However, if pigment is included in the wood treatment composition and/or in a transparent stain, the amount of pigment should be carefully controlled such that the natural grain and individual surface appearance variations, etc. of the wood substrate remains visible after application and drying. When it is desired to employ a pigment for the purpose of modifying the color of the wood substrate while still allowing the natural grain, etc. to remain visible, any pigment compatible with the treatment composition may be employed. Such pigments are well known in the art. When pigment is utilized, typically it is first formed as a concentrate having the consistency of a paste containing the pigment and a suitable grind vehicle. Any compatible grind vehicle may be used. Further, assuming they are compatible, commercially available predispersed pigments may be incorporated into the wood treatment composition. The amount of pigment present in the pigment paste is determined by the strength of color desired from the ultimate wood treatment composition with due consideration being given to providing for visibility of the natural appearance of the wood but for color modification. The paste may include minor amounts of such components as grinding agents, antisettling agents and solvent. Typically, when pigment is utilized, wood substrate color can be modified while allowing surface visibility when pigment paste is added to the wood treatment composition at a level of from 3 to 10 percent by weight, based on the weight of the wood treatment composition.

Suitable water repellents which can be incorporated in the treatment composition include various materials known in the art for this purpose, such as paraffin wax, polybutene resins such as those available from S and S Chemical Company, Inc., silicone fluids such as that available from Dow Corning Corporation under the tradename DC 200, silicone polymers such as that available from Dow Corning Corporation under the tradename DC1107, silicone resins such as that available from Union Carbide Corporation under the tradename R270, silicone waxes such as that available from Union Carbide Corporation under the tradename L-49 and poly-oxo-aluminum stearate available as MANALOX 403/60 from Manchem Corporation. It should be understood that high levels of water repellent in the wood treatment composition can interfere with the application of the transparent topcoat to the surface of the treated wood.

Preferred water repellents include an alpha olefin having 20 to 24 carbon atoms, a blend of said alpha olefins, a similar paraffin blend, or a mixture thereof, with the alpha olefin blend being preferred, as described in U.S. Pat. No. 4,360,385 and 4,404,239. The individual cuts of alpha olefin having 20 to 24 carbon atoms are also useful, though such cuts are not readily available and are generally less preferred for this reason. The preferred olefin and paraffin blends are characterized by a narrow range of carbon compounds. That is, while paraffins are well known and have been used extensively heretofore, such materials are blends of a wide range of different carbon chain length materials- These commonly used paraffin blends make application of the transparent topcoat difficult and do not provide the good water-repellency efficiencies of the olefin and paraffin compounds described in U.S. Pat. Nos. 4,360,385 and 4,404,239. Narrow cuts of olefin and/or paraffin provide good results in terms of the water-repellency they are able to impart to wood. At least about 50 percent by weight of the olefin blend or paraffin blend comprises compounds having from 20 carbon atoms to 24 carbon atoms. Preferably, the olefin blend and paraffin blend contain at least about 70 percent by weight, and, more preferably, at least about 90 percent by weight of the compounds having between 20 and 24 carbon atoms. The most preferred blend contains at least about 96 percent by weight of the compounds having 20 to 24 carbon atoms and less than about 3 percent by weight of the compounds having less than 20 carbon atoms and less than about 1 percent by weight having more than 24 carbon atoms.

Any of the known compounds which are useful as wood preservatives (such as, for example, biocides, fungicides, and/or algicides) and which are compatible with the other components of the wood treatment composition can be used as the wood preservative herein. Examples of such materials include organic tin compounds such as triphenyl and tributyl tin oxide, chlorinated compounds such as tri-, tetra-, and pentachlorophenol, mono- and dichloro naphthalenes, organic mercury compounds such as phenyl mercury acetate and oleate, and 3-iodo-2-propynl butyl carbamate. Preferably the wood preservative is present in the wood treatment composition at a level of from about 0.55 percent to about 6.0 percent, more preferably from about 0.55 percent to about 3.0 percent, by weight of the composition. Preferably, the wood preservative is present in the wood treatment composition at a level equal to or exceeding the "threshhold concentration" of the wood preservative as determined by the NWMA-M-81 soil block test published by the National Wood Window and Door Association.

Film-forming resins have conventionally been used in wood treatment compositions to provide a degree of water-repellency and to aid paint holdout. A minor amount of film-forming resin optionally can be incorporated in the wood treatment compositions for the method of the invention. Suitable film-forming resins are those which do not substantially react with the organosilicon-containing compound. Thus, a substantial amount of the organosilicon-containing compound present in the wood treatment composition is free to penetrate the surface of the wood. Examples of such resins include conventional alkyd resins (including urethane alkyd resins), acrylic resins, vinyl resins, epoxy resins, silicone resins, polyester resins and polyurethane resins.

Other conventional additives optionally may be included in the wood treatment compositions such as surfactants, ultraviolet absorbers (or stabilizers) topcoat catalysts. Typically, when present, these additives are utilized at a level of less than about 5 percent by weight of the composition.

Because of the nature of wood substrates, of conventional pretreatments, of conventional clear coating systems and of the environmental factors involved in the weathering process, wood protection systems employing conventional clear coatings, even in combination with conventional pretreatments, generally have not been satisfactory with respect to simultaneously providing long term weathering resistance to the wood substrate itself and also long term weathering resistance of the clear coating. Typical manifestations of wood substrate failure include bleaching, discoloration and "grain raising." Typical manifestations of failure of the clear coating itself include cracking, peeling and lifting from the substrate. As can be appreciated, for example from consideration of the articles referred to above, this objective of achieving simultaneous long term protection of wood from weathering and permitting the natural beauty of the wood substrate to remain readily visible, has been exceptionally difficult and heretofore not achieved. Applicants have discovered that utilization of the method of the present invention involving application of a pretreatment composition as previously described in combination with application of a transparent film-forming coating composition having certain characteristics, can result in attainment of this elusive goal.

Other additives useful for wood preservation, as described in U.S. Pat. No. 4,913,972, which is incorporated herein by reference, can be used simultaneously with or in a separate application step to the application of the siloxanes used herein. Such additives can be, for example, a wood preservative, hiding tints or pigments, ultraviolet light absorber and insecticides. If the application of these or other additives is with the siloxanes of this invention, the additives should be at least partially soluble in water or in the siloxane compositions.

The stable aqueous compositions of this invention can be applied exactly as described in the Grunewalder et al patent identified above, again whose disclosure is incorporated herein by reference, and, can be applied alone as the only treatment to preserve wood, but, more preferably, are applied in conjunction with other separate treatments, such as a hydrophobic wood preservative composition described in column 18, lines 48 to 58, of Grunewalder et al and a urethane topcoat as described in Example 3 of Grunewalder et al.

DESCRIPTION OF PREFERRED EMBODIMENTS

Example 1

To a glass reactor with a nitrogen atmosphere 62.4 grams of benzylamine was charged and heated to 50° C. Then 137.6 grams of glycidoxypropyl trimethylsilane was added dropwise over a period of two hours. Heating was continued at 50° C. for three hours, when the temperature was raised to 80° C. After one hour at 80° to 85° C., the epoxy equivalent weight was 4031. To 195 grams of the above product at 30° C. there was added 121.9 grams of octenylsuccinic anhydride dropwise over 1.6 hours. The reaction was exothermic and the temperature increased to 40° C. When the temperature dropped to 35° C., the contents were heated to 60° to 65° C. for one hour. Then 20.6 grams of isopropanol was added to reduce the viscosity, and the product was cooled. The acid number was 96.0, the infrared spectrum showed no anhydride remaining and the amine equivalent weight was 1378.

Twenty grams of the above solution was added to a stirred mixture of 3.46 grams of triethylamine and 23.5 grams of dionized water. A clear solution resulted, which was 40 weight percent solids and 100 percent neutralized.

A similar solution to that above passed a hot storage accelerated stability test of 120° F. for three days with no apparent change. A similar dispersion with sonia as neutralization agent instead of triethylamine at 10 weight percent solids, instead of 40 weight percent solids, was still very fluid, but had some sediment in the bottom of the sealed jar after three days. At 125° F. Therefore, the triethylamine neutralizer performs better, yielding a more stable product than sonia in this comparison.

Example 2

To 382 grams of bis(trimethoxysilylpropyl)amine was added portion-wise over 1.5 hours to 148 grams of phthalic anhydride at between 24° and 70° C. Some heat was applied to begin the exothermic reaction at the early stages. The reaction rate and the temperature of 55° to 70° C. were then maintained by adding the phthalic anhydride, with only slight heating required. The product was then cooled, after which 33.2 grams of isopropanol was added to reduce viscosity. The product had an acid number of 102.9 and an amine equivalent weight of 17. No anhydride was present by infrared analysis.

The reaction product was dispersed into 23.3 grams of water and 3.71 grams of triethylamine to form a hazy dispersion (40 weight percent solids and 100 percent neutralized), which gelled in about two minutes. A dispersion using ammonia in place of triethylamine gave a poorer dispersion, which also gelled. Even at 10 weight percent solids the dispersion was poor. This shows that an aminodisilane carrying a six carbon hydrophobic group will not give a stable aqueous solution.

Example 3

To 223 grams of N(beta-aminoethyl)-gamma-aminopropyltrimethoxysilane in a flask equipped with a stirrer and nitrogen atmosphere there was added dropwise over four hours 196 grams of a 50 weight percent solution of maleic anhydride in ethyl acetate. During the addition, 138.2 grams of ethyl acetate was added to reduce viscosity. The maximum temperature was 43° C. Then 253 grams of dodecenyl succinic anhydride was added dropwise over 1.5 hours. After 0.5 hour more, anhydride was still present, and the amine content was 0.69 meq/gram. The reaction mixture was heated to 50° to 55° C. and held for 4.75 hours. No anhydride remained, and the residual amine content was 0.34 meq/-gram. The acid value of the amide-acid product was 137.

100.64 grams of the above composition was mixed with 21.1 grams of triethylamine (84 percent neutralization) which reacted exothermically to provide the amine-acid salt. Then 93.4 grams of water was added and the mixture again exothermed when the sample was mixed, again to about 45° C. maximum. The product was theoretically 38.8 weight percent solid (actual 37.4 weight percent solids measured by evaporating about one gram for one hour at 110° C.). The Gardner-Holdt viscosity was A when measured the following day.

Example 4

A two-liter reactor equipped with a stirrer, reflux condensor, thermocouple and nitrogen atmosphere was charged with 223 grams of N(beta-aminoethyl)-gamma-aminopropyl-trimethoxy silane. By means of an addition funnel, 443 grams of dodecenyl succinic anhydride was added dropwise with stirring over 5.75 hours. The exotherm produced a maximum temperature of 46° C. During the addition, after about one-third of the addition, 91 grams of dry ethylacetate was added to reduce the increasing viscosity. At about half way through the addition, 158 grams of additional ethyl acetate was added- Thirty minutes after the addition was complete, the amine content was 0.7 meq/gram and a small amount of anhydride remained as observed from an infrared spectrum. After heating to 50° C. for 1.25 hours, no anhydride remained, the amine content was 0.65 meq/gram. The acid value was 91.0.

106.0 grams of the above product and 20.9 grams of triethylamine (89 percent neutralization) were mixed. Then 93.0 grams of water was mixed in. The maximum temperature of mixing was 40° C. The next day following mixing the product, a clear brown solution, had a Gardner-Holdt viscosity of B, and an analyzed solids content of 32.1 weight percent (110° C./one hour).

Example 5

To a nitrogen blanketed reactor containing 23.4 grams of gamma-amino propyltrimethoxysilane and 13.2 grams of triethylamine there was added portionwise with stirring 9.32 grams of ortho-sulfobenzoic anhydride. The mixture was reacting slowly as evidence by a mild exotherm. Then 39.9 grams of acetonitrile was added to eliminate the heterophase mixture. However, a slurry remained. Portionwise additions of sulfobenzoic anhydride continued with exotherm as high as 55° C. until a total of 27.4 grams of sulfobenzoic anhydride had been added over about 1.5 hours total. The acid value of the resulting slurry was 104.2. The amine content by HCl titration was 0.85 meq/gram.

To 19.1 grams of deionized water was added with stirring 29.66 grams of the above solution. A clear solution resulted which was orange-brown. The solution had a pH of 8.25 and a measured solids content (by evaporation of about one gram sample at 110° C. for one hour) of 31.2 weight percent solids.

Example 6

A. To a two-liter flask equipped with a nitrogen sparger an addition funnel and stirrer, there was charged 747 grams of dodecenylsuccinic anhydride. Then 452.8 grams of gamma-aminopropyltrimethoxysilane was added dropwise with stirring over a period of 1.8 hours. The temperature of the mixture reached 60° C. during the addition. Following the subsidence of the exotherm, the acid number was 128, and the amine equivalent weight was 6160. No anhydride was detected by infrared analysis and C═O absorbtions were present at 1635 and 1705 cm-1, indicating the presence of amide and acid groups. To 320.2 grams of the above product was added 74.0 grams of triethylamine. The density of the product was found to be 8.224 pounds per gallon and the solids content 73.0 weight percent. This product (350 grams), containing a hydrophobic dodecenyl moiety and an anionic water-solubilizing moiety (an amine salt of a carboxylic acid) was added to 284.3 grams of water to produce a clear aqueous solution containing 45 weight percent of the new product claimed herein, which hydrolyzed to a solution of 40.2 weight percent of calculated solids having Si—O—Si bonding.

B. In a glass reactor, 1 mole of dodecenylsuccinic anhydride and 1 mole of gamma-aminopropyltrimethoxysilane were mixed and allowed to exotherm. The temperature reached approximately 90° C. The resulting acid was neutralized with triethylamine (1 eg. per 1 eg. acid). The product was poured into water to give a 45% solution in water. The Gardner-Holdt viscosity was Y-, the acid value was 48.3.

Example 7

116.85 grams of iso-octadecenylsuccinic anhydride and 59.77 grams of gamma-aminopropyltrimethoxysilane were combined in a reactor with stirring and allowed to exotherm. When the mixture reached ambient temperature, 33.73 grams of triethylamine was added thereto. The resulting product had a Gardner-Holdt viscosity of V+, a Gardner color of 3–4 and an acid value of 50.6, consistent with an acid group being present. An infrared spectrum of the product showed no remaining anhydride. The product obtained was an amine-neutralized amide-acid silane with hydrolyzable methoxy groups. Some cyclic imide was likely also present. The isooctadecenyl group serves as the hydrophobic moiety, and the neutralized acid serves as the water-solubilizing group.

Example 8

To a 250 milliliter flask there was added 121 grams (0.05 mole) of Igepal CO 970 [nonylphenoxypoly(ethyleneoxy) ethanol, obtainable from GAF Corporation] and the contents thereof were warmed with nitrogen to 55° C. Then 12.35 grams of isocyanatopropyltriethoxysilane was added with stirring. Following this, 0.133 gram of dibutyltin dilaurate catalyst was added, and the mixture was heated to 90°–95° C. and held at this temperature level for about two hours. No isocyanate was present by infra-red analysis. The product was a waxy solid after cooling to ambient temperature. The compound obtained was a urethane-silane containing a water-solubilizing poly(oxyethylene) group. The nonyl phenyl group serves as the hydrophobic moiety.

To 26.3 grams of the above compound there was added 26.3 grams of water, and the mixture was stirred and warmed to dissolve the compound. The following dilutions were made:

| Grams of Above Mixture | Grams of Water | Weight Percent Solids |
|---|---|---|
| 10.0 | 2.25 | 40 |
| 5.0 | 5.0 | 25 |
| 5.13 | 11.97 | 15 |
| 5.0 | 50 | 5 |

Each of these solutions was found to be stable, in that no change in physical condition of the solutions occurred, on storage at 120° F. for 27 days.

Example 9

The 3-aminopropyltrimethoxysilane (339.9 g) was added dropwise to the octenylsuccinic anhydride (600.1 g, acid no. 269.1) allowing the temperature to rise to about 42° C. An additional 18 g of the aminosilane was then added, then the product heated to 60° C., then cooled. The product acid value was 145.4. The amide-acid product was neutralized and diluted with water simultaneously by pouring 8 g into a solution of 1.87 g dimethylethanol amine and 30.1 g water. A clear solution resulted.

Example 10

To a nitrogen padded flask there was charged 291.8 grams of methylhexahydrophthalic anhydride and then 308.2 grams of gamma-aminopropyltrimethoxysilane was added dropwise over a period of about four hours. The maximum temperature of the exotherm was 66° C. The final acid number was 130.6, and the amine equivalent 2308. An infra-red spectrum showed no remaining anhydride. The acid generated from the reaction was neutralized with triethylamine. The product obtained was an amine-neutralized amide-acid silane. The methylcyclohexylidene moiety serves as the hydrophobic moiety and the amine-neutralized acid serves as the water-solubilizing group.

Example 11

A portion of the amide-acid product of Example 3 was neutralized with ammonium hydroxide (one mole of ammonium hydroxide per equivalent of acid) by pouring the amide-acid into water containing the ammonium hydroxide. The final solids was 38.1%. The viscosity (Gardner-Holdt) was A.

Example 12

To a glass reactor was added:

23.6 g glycidoxy propyltrimethoxysilane
21.3 g dimethyldodecylamine
30.1 g anhydrous methanol
6.23 g glacial acetic acid A mild exotherm resulted on mixing. The contents were heated to 55° C. for 5 hours. The epoxy equivalent weight was 7818. An additional 4 hours at 55° C. produced a product with epoxy equivalent weight of 16,000. Additional 55° C. heating for about 8 hours gave a product with no remaining epoxide. The structure of the product is believed to be:

$$[CH_3(CH_2)_{11}\overset{+}{N}(CH_3)_2-CH_2CH(OH)CH_2OCH_2CH_2CH_2Si(OCH_3)_3]CH_3CO_2^-$$

Then 40.5 g of the stable liquid produced above was added with stirring to 40.5 g deionized water. A yellow solution was formed with Gardner Holdt viscosity of <A (theoretically 27.6% solids). The calculated silicon content was 3.12%.

Example 13

A stain containing a siloxane wood preservative of this invention was prepared by stirring together the following ingredients:

15.0 grams of the product of Example 6B above,
90.4 grams of dionized water,
0.35 grams of a defoaming surfactant and
4.0 grams of the tint paste described below.

Tint Paste

A tint paste was prepared by grinding together the following:

8 parts by weight of carbon block
270 parts by weight of yellow iron oxide
50 parts by weight of red iron oxide
185 parts by weight of deionized water
7.4 parts by weight of defoaming surfactant[1]
1.4 parts per by weight of Tinuvin 1130 light stabilizer[2]
200 parts by weight of water based acrylic grind resin[3]

[1]Surfynol 104, an acetylenic diol available from Air Products
[2]Available from Ciba-Giegy
[3]A 39 weight percent aqueous solution of an acrylic polymer containing about 12 weight percent acrylic acid Pine blocks (4"×12"×1") and luan blocks (6"×12"×1") were dipped into a preservative treatment similar to that used in U.S. Pat. No. 4,404,239, Example 2, for about 30 seconds. The blocks, following draining and drying overnight, were then sprayed on one side with (1) the siloxanepreservative stain prepared above, (2) with a silane and solvent-based stain of U.S. Pat. No. 4,913,972, Example 8b, or (3) with no silicon composition and only stain for comparison. The above sprays produced a wet film thickness of about 4 mils, which rapidly soaked into the wood.

After standing at ambient temperature overnight, topcoats were applied as follows (to the face of the board treated with the stains above):

Solutions of polyurethane precursors similar to those used in Example 3 of U.S. Pat. No. 4,913,972 were prepared at 40 weight percent solids and at 56 weight percent solids. Solvents used for the dilutions were methyl amylketone, xylene, and oxyhexyl acetate. The first coat at 40 weight percent solids was sprayed at 1.5–2 mils wet film thickness, which was flashed 10 minutes at ambient temperature and followed by spraying the 56 weight percent solution of the same polyurethane composition. The boards were then flashed 10 minutes at ambient temperature, followed by baking at 120° F. for 20 minutes to cure the urethane formulation. Thus two types of wood were treated identically with and without siloxane or silane preservatives. Two boards of each type were treated and placed on exposure.

After two years in Florida, South 45° exposure, of the above pine and luan boards with control boards comparing no silane or siloxane treatment, the following results were observed:

| Board Number | |
|---|---|
| Pine Board, Controls (No Silane or Siloxane) | |
| One | No failure, film integrity good |
| Two | Crack in board and coating |
| Pine Board, With Siloxane of this Invention | |
| One | No failure, good film performance |
| Two | No failure, good film performance |
| One | Discontinued test due to mildew spotting |
| Two | Discontinued test due to mildew spotting |
| Pine Board, With Siloxane of U.S. Pat. No. 4,913,972 | |
| One | No failure, good film performance |
| Two | No failure, good film performance |
| Luan, Control (No Siloxane or Silane) | |
| One | Discontinued test due to mildew spotting |
| Two | Discontinued test due to mildew spotting |
| Luan, With Siloxane of this Invention | |
| One | No failure, good film performance |
| Two | No failure, good film performance |
| Luan, With Silane of U.S. Pat. No. 4,913,972 | |
| One | Discontinued due to mildew spotting |
| Two | Discontinued due to mildew spotting |

Good film integrity was observed for the products of this invention, and no film failures were recorded. In this test with luan, the siloxane treated boards outlasted even the boards treated with the silanes of U.S. Pat. No. 4,913,972.

Example 14

Similar comparisons were done on 4"×2½"×1" pine boards. The coated face of these boards was exposed to 5000 hours accelerated weathering using an Atlas Weather-o-Meter using the following conditions:

Irradiance Level: 0.35 watts/meters², 340 nm
Temperature: 70° C.
Light Cycle: 108 minutes light only, 12 minutes of light and water The results are summarized below:

| Board Description | Observations after 500 Hours |
|---|---|
| 1. Pine control (no | Trace of white streaks |

-continued

| Board Description | Observations after 500 Hours |
|---|---|
| siloxane or silane) | |
| 2. Pine (silane of Example 6, U.S. Pat. No. 4,913,972) | One white spot |
| 3. Pine control (no siloxane silane) | One large white bubble (1" × 1/2") |
| 4. Pine (siloxane of this invention) | One small bubble - good film integrity |

White streaks are believed to be the worst for clear coat appearance, followed by bubbles which cause film delamination, followed by small bubbled, followed by white spots which are least obvious.

Examples 15 through 20

The products of the noted examples (see Table 1 below) were diluted with water, and spray applied as in Example 13 above to give blocks (4"×12"×1") which had been previously treated with the preservative of U.S. Pat. No. 4,404,239, Example 2 (by dipping the board into the preservative for 30 seconds), then dried overnight.

Then after overnight drying, the treated blocks were coated with polyurethane as in Example 13 and exposed to the weatherometer as in Example 14 above.

The results are described in Table 1 below.

TABLE 1

| EXAMPLE | PRODUCT OF EXAMPLE | DILUTED WITH WATER TO THE SOLIDS | % BLEACHING* OBSERVATIONS AFTER 857 HRS. WEATHEROMETER EXPOSURE | RELATIVE COATING PERFORMANCE OF SILOXANE TREATED COATINGS (1 BEST) |
|---|---|---|---|---|
| 15 | 9 | 3.7 | 10 | 1 |
| 16 | 7 | 10 | 20 | 3 |
| 17 | 6A | 5 | POOR | NOT RATED |
| 18 | 1 | 10 | 20 | 2 |
| 19 | ORGANOSILANE SOLUTION OF EXAMPLE 6, U.S. PAT. NO. 4,913,972 | USED AS IS | 15 | NOT RATED |
| 20 | NO SILANE OR SILOXANE | | TRACE | NOT RATED |

*The fully coated boards were also crosshatched (cut through coating by 11 sharp metal blades in 0.1 inch apart parallel strips and overcut orthoganally also in 0.1 inch apart parallel strips to form a "checkerboard" pattern of cuts prior to weatherometer exposure).

Bleaching is measured as the percent of whitened area of the wood within the crosshatch area (1 inch square). The higher the bleaching number, the poorer the coating.

The performance of the siloxane treated samples was essentially equivalent to the organosilane treatment of U.S. Pat. No. 4,913,972, Example 6. These coatings were rated (see Table 1) by a coatings expert considering their appearance after exposure, considering appearance both inside and outside the crosshatch area, and considering all factors as to which would produce the best overall coating, but using only the available accelerated weathering data provided by the weatherometer study.

Examples 21 through 25

A series of pine boards (4"×12"×1") was prepared with a preservative pretreatment similar to that used in Example 2 of U.S. Pat. No. 4,404,239 by dipping 30 seconds as described in Example 13 above.

Aqueous dilutions of the siloxanes of the examples noted in Table 2 were applied as described in the previous set of examples (in Table 1).

The samples were then topcoated after drying overnight according to the procedure of Example 3, U.S. Pat. No. 4,913,972. The coated boards were crosshatched as described in the series of Examples above, then exposed to the weatherometer, set as in Example 14 above. Results are provided in Table 2.

TABLE 2

| EXAMPLE | PRODUCT OF EXAMPLE | CONCENTRATION OF SILOXANE IN WATER AT APPLICATION | % BLEACHINGS* OBSERVATIONS AFTER 1,785 HRS. WEATHEROMETER EXPOSURE | COATING IMPERFECTIONS |
|---|---|---|---|---|
| 21 | 8 | 5% | <10% | TRACE |
| 22 | 11 | 10% | 40% | POOR |
| 23 | 3 | 10% | <5% | GOOD |
| 24 | 12 | 10% | <10% | TRACE |
| 25 | SILANE TREATMENT OF U.S. PAT. NO. 4,913,972, EXAMPLE 6 | | <10% | TRACE |

Example 26

This example illustrates neutralization with a quaternary ammonium hydroxide, and two different amines.

The reaction product of octenylsuccinic anhydride (1 mole), and 3-aminopropyltrimethoxy silane (1 mole) [amide-acid of Example 9], 8.0 g, was poured into water 18.32 g containing 13.63 g of tetrabutylammonium hydroxide (40% in water). The product (20% theoretical solids) was a clear solution.

The octenyl succinic anhydride 3-aminopropyltrimethoxy silane amide-acid adduct of Example 9 was also neutralized (at 100% neutralization, meaning one equivalent of amine per equivalent of acid in the adduct) in individual experiments with 2-amino-2-methyl-1-propanol, and with ammonia. In each case the 20% solids products were clear solutions.

Obviously, many modifications and variations of the invention, as hereinabove set forth, can be made without departing from the spirit and scope thereof, and therefore only such limitations should be imposed as are indicated in the appended claims.

We claim:

1. Stable aqueous dispersions having a particle size in the range of about 10 to 200 nanometers of silanes selected from the group of silanes having the following structural formulas:

$$R^1SiY_3 \quad (I)$$

and $$R^1R^2SiY_2$$

wherein $R^1$ represents a hydrocarbon group having from about 7 to about 30 carbon atoms containing at least one hydrophobic moiety and at least one neutralized anionic water-solubilizing moiety;

$R^2$ represents $R^1$, H, an alkyl radical having from 1 to 20 carbon atoms, an aryl radical having 6 to 18 carbon atoms, an aralkyl radical or an alkaryl radical having from 7 to 20 carbon atoms;

Y represents $OR^3$, with $R^3$ representing H, a lower alkyl having from 1 to 3 carbon atoms, aryl radicals or alkaryl radicals having from 6 to 10 carbon atoms or $$-\overset{O}{\overset{\|}{C}}-R^4$$

wherein $R^4$ represents H or a lower alkyl having from 1 to 2 carbon atoms, said dispersions being stable for at least 20 days without externally added surfactant.

2. The stable aqueous dispersions of claim 1 wherein $R^1$ has from about 7 to about 20 carbon atoms;

$R^2$ represents $R^1$, H, an alkyl radical having from 1 to 10 carbon atoms, an aryl radical having from 6 to 10 carbon atoms, an aralkyl radical having from 7 to 20 carbon atoms or an alkaryl radical having from 7 to 10 carbon atoms.

3. The stable aqueous dispersions of claim 1 wherein the silane dispersed therein is the silane represented by structural formula I.

4. The stable aqueous dispersions of claim 1 wherein the silane dispersed therein is the silane represented by structural formula (II).

5. The stable aqueous dispersions of claim 1 wherein said dispersions contain from about 5 weight percent to about 60 weight percent of said silanes and their hydrolysis products.

* * * * *